United States Patent [19]
Burr et al.

[11] Patent Number: 5,318,043
[45] Date of Patent: Jun. 7, 1994

[54] CONDOM FOR ORAL-GENITAL USE

[76] Inventors: Lawrence S. Burr, 76 Manzanita Rd., Fairfax, Calif. 94930; Kenneth Matsumura, P.O. Box 5313, Berkeley, Calif. 94705

[21] Appl. No.: 422,108

[22] Filed: Oct. 16, 1989

[51] Int. Cl.[5] ............................................. A61C 5/14
[52] U.S. Cl. .................................... 128/859; 128/844
[58] Field of Search ................ 604/327, 328, 346, 347; 128/842, 844, 859, 857; 206/69

[56] References Cited

U.S. PATENT DOCUMENTS

| | | | |
|---|---|---|---|
| 1,986,988 | 1/1935 | Treadwell | 128/857 |
| 3,682,164 | 8/1972 | Miller | 128/857 |
| 3,692,025 | 9/1972 | Greenberg | 128/857 |
| 4,304,227 | 12/1981 | Samelson | 128/857 |
| 4,805,604 | 2/1989 | Spery | 604/347 |
| 4,872,464 | 10/1989 | Loeb et al. | 128/844 |
| 4,888,007 | 12/1989 | Loeb et al. | 128/844 |
| 4,949,731 | 8/1990 | Harding | 128/844 |

FOREIGN PATENT DOCUMENTS

| | | | |
|---|---|---|---|
| 274352 | 9/1990 | Canada . | |
| 1026044 | 3/1958 | Fed. Rep. of Germany | 128/844 |
| 3644344 | 7/1988 | Fed. Rep. of Germany . | |
| 1163130 | 11/1956 | France | 604/346 |
| 8806029 | 8/1988 | World Int. Prop. O. | 604/347 |
| 8901768 | 3/1989 | World Int. Prop. O. | 128/844 |

Primary Examiner—Randall L. Green
Assistant Examiner—Rob Clarke
Attorney, Agent, or Firm—David Fink

[57] ABSTRACT

A condom designed for oral-genital sex includes, in one aspect, a device adapted to be worn in the mouth of the person practicing oral sex. The device includes a tubular member having one closed end and formed of thin, pliant, impervious material. Joined to the open end of the tubular member are two or three flanges extending generally radially outwardly and spaced closely together. The flanges are curved out of a plane transverse to the axis of the tubular member to define a channel adapted to receive the upper and lower lips of an average person. The device is gripped by placing the lips within the channel, and closing the jaws slightly to compress and retain the open end of the device. The tubular member may be formed to extend into the mouth of the wearer, for the purpose of performing fellatio. A penis may be inserted into the tubular member without making contact with the lips or mouth or tongue of the wearer. In an alternative form of the invention, the tubular member may extend outwardly from the flanges and the mouth, so that the tongue of the wearer may be extended into the tubular member to perform cunnilingus without making direct contact with the vulva. In another aspect of the invention, there is provided a shield formed as a planar oval from pliant, impervious material, the shield being shaped and adapted to be placed over the genital area. The shield includes a central opening from which a tubular condom extends, so that the assembly may be employed for oral sexual contact as well as intercourse without the risk of skin-to-skin contact. In a modification of this embodiment, the shield is provided as a separate component, with a flange surrounding the central opening. The flange is provided with means for engaging and sealing with the outer circumferential edge portion of a typical prior art male condom, so that the shield may be joined temporarily to a commercially available condom for the practice of safe sex.

15 Claims, 5 Drawing Sheets

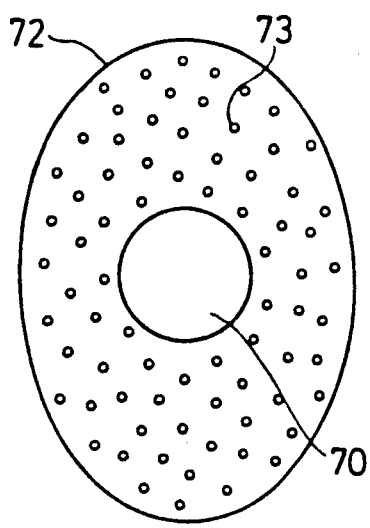
FIG. 11
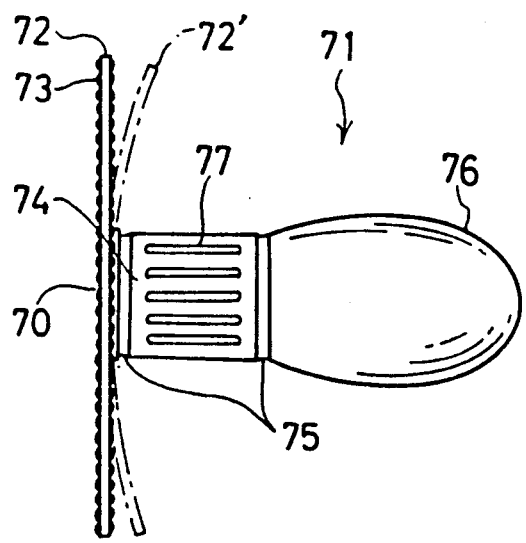
FIG. 12
FIG. 14
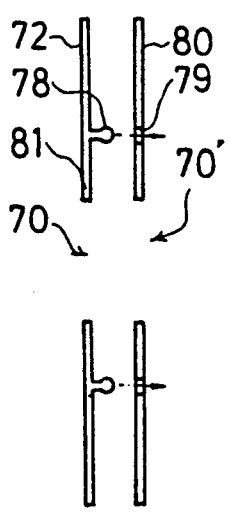
FIG. 13
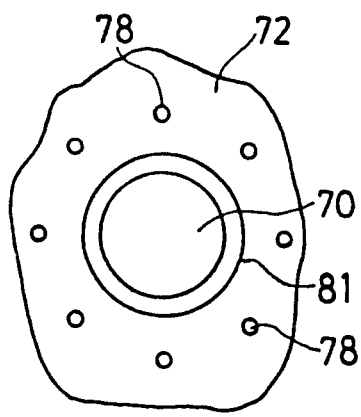
FIG. 15
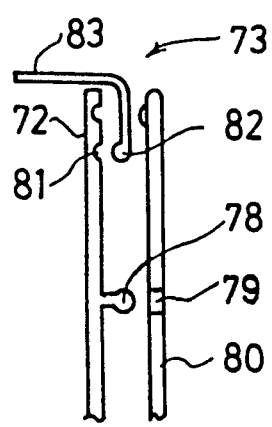
FIG. 16
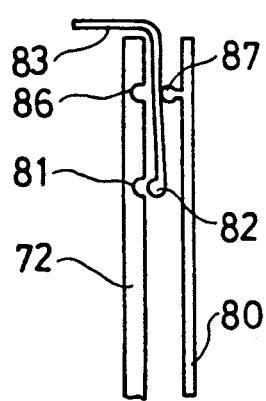
FIG. 17
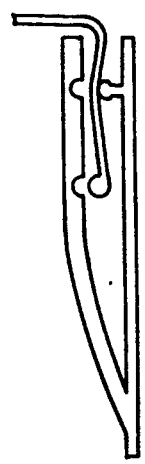

CONDOM FOR ORAL-GENITAL USE

BACKGROUND OF THE INVENTION

In recent years, the appearance of the HIV virus and the impending Acquired Immune Deficiency Syndrome epidemic have created an atmosphere of fear, caution and prudence in which sexually active adults must consider protecting themselves from infection by HIV virus as well as other venereal diseases. It is generally accepted as fact that the condom provides the best protection from venereal disease and HIV virus, aside from complete sexual abstinence. Unfortunately, such a positive barrier device is, at present, the only sure or certain way to prevent transmission of all STDs, many of which cause great personal suffering and, in the cases of AIDS and syphilis, death.

Condoms are generally designed to be applied to the male member, although recent adaptations have been introduced which permit their use by women in the form of a liner for the vaginal canal. However, a significant form of sexual activity, namely oral-genital sexual contact, has not been well served by the forms of condoms known in the prior art. Although many individuals do not openly discuss or acknowledge participating in such practices, many surveys have shown that oral-genital sex is highly desired and engaged in frequently. Commercially available condoms are not designed to facilitate or accommodate oral-genital sex. Moreover, the oral cavity, together with the lips and surrounding skin, provides many opportunities for disease transmission. Brushing and flossing of teeth, biting the cheek or tongue accidentally, or STD lesions in the mouth and throat areas all create breaks in the skin and mucosa that provide direct vectors to the blood. The present invention is directed toward a condom-like prophylactic that protects the oral cavity during oral sexual activity, so that disease transmission is blocked. It also protects the genitals, thus avoiding transmission in either direction. This is a unique solution to a very serious problem.

The typical male condom device may be used to prevent skin-to-skin contact during fellario, but it suffers from the same drawback for this use as for other uses; i.e., it requires male arousal prior to use, so that the condom may be applied to the male member. If arousal can be achieved only through sensual contact, then the safety desired by the user of the condom may have been abrogated. Moreover, the typical male condom is required to engage the penis in a tight, compressive grip to prevent accidental removal during vaginal sex; this tight fit is undesirable for fellatio and uncomfortable for the fellatee.

Furthermore, the condoms known in the prior art are not designed to protect against skin-to-skin contact during cunnilingus. Devices have been invented to protect a person's tongue from contact with unpalatable medicine, as well as other devices such as impervious sheets and garments, but none of these inventions permit the practice of cunnilingus while eliminating the risk of disease transmission through direct contact. This is a major failing of the prior art, especially since many individuals participate in cunnilingus without protection, and such practices can be a major vector of disease transmission.

From a commercial standpoint, surveys have shown that nearly 50% of condoms purchased are sold to women, although it is clear that condoms as known in the prior art are predominantly worn by the male. Therefore there is an implication that many women are concerned about contraception and disease prevention, and desirous of taking steps toward prevention of both. Many persons of both sexes may wish to participate in oral sex but hesitate. These "aesthetically fastidious" individuals may now safely and pleasurably benefit themselves and their sex partners, using the present invention. Studies show that only 50% of women achieve orgasm via penile/vaginal sex. One-half require oral or digital manipulation to achieve climax. Indeed, at present a woman who desires to achieve a climax via cunnilingus must do so unprotected. Combined with the fact that many women desire to participate in cunnilingus and fellatio, clearly there is an unfilled need and a large market for condoms which permit the safe practice of oral sex.

It should also be noted that condoms currently available on the market are not designed nor directed toward oral use. The lubricants typically provided in condom packages have odors and tastes that are at best inoffensive, and at worst are completely aversive.

SUMMARY OF THE PRESENT INVENTION

The present invention generally comprises a condom-like prophylactic designed to permit the practice of oral sex while preventing the transmission of venereal and other contagious diseases through oral-genital contact. In one aspect of the invention, there is provided a device adapted to be worn in the mouth of the person practicing oral sex. The device includes a tubular member having one closed end and formed of thin, pliant, impervious material. Joined to the open end of the tubular member are a pair of flanges extending generally radially outwardly and spaced closely together. The flanges are curved out of a plane transverse to the axis of the tubular member to define a channel having the general configuration of the lips and mouth of an average person. The device is gripped by placing the lips within the channel, and closing the jaws slightly to compress and retain the open end of the device. A third flange may be provided, generally parallel to the other flanges, to define a further channel in which the teeth of the user may be engaged.

The tubular member may be formed to extend into the mouth of the wearer, for the purpose of performing fellatio. A penis may be inserted into the tubular member without making direct contact with the lips or mouth or tongue of the wearer. In an alternative form of the invention, the tubular member may extend outwardly from the flanges and the mouth, so that the tongue of the wearer may be extended into the tubular member to perform cunnilingus without making direct contact with the vulva.

In a further embodiment of the invention, there is provided a shield formed as a planar oval from pliant, impervious material, the shield being shaped and adapted to be placed over the genital area. The shield includes a central opening from which a tubular condom extends, so that the assembly may be employed for oral sexual contact as well as vaginal-penile intercourse without the risk of skin-to-skin contact. In a modification of this embodiment, the shield is provided as a separate component, with a flange surrounding the central opening. The flange is provided with means for engaging and sealing with the outer circumferential edge portion of a typical prior art male condom, so that the shield may be joined temporarily to the condom for the practice of safe sex. The outer circumferential edge of the condom may be rolled or unrolled to provide the desired length, and the edge-engaging means retains the unrolled portion. After use, the condom may be removed and discarded, and the shield may be either discarded or cleaned and subsequently reused.

The invention also includes an embodiment in which the condom is provided with a progressively expanding diameter from the base to the closed end. The expanded head provides far more comfort and sensation during fellatio.

In all of the embodiments described, the device may be packaged not only with a lubricating substance but also or alternatively with a substance that imparts a pleasant scent and taste to the device, adding further sensual pleasure to oral sexual activity. In addition, the pliant material that forms the condom-like prophylactic may be provided with surface texture and color to enhance enjoyment during use.

BRIEF DESCRIPTION OF THE DRAWING

FIG. 11 is an end view of another embodiment of the present invention, including a shield and adapted for use in both oral sex and intercourse.

FIG. 12 is a side elevation of the embodiment of the invention shown in FIG. 11.

FIG. 13 is a fragmentary plan view of a further embodiment of the shield aspect of the present invention, showing a sealing arrangement for engaging and sealing with a typical prior art male condom.

FIG. 14 is a side view of the embodiment of FIG. 13, showing the sealing means for engaging a male condom.

FIG. 15 is a side view as in FIG. 14, showing a further sealing means for engaging a male condom.

FIG. 16 is a side view as in FIG. 14, showing another sealing means for engaging a male condom.

FIG. 17 is a side view as in FIG. 16, showing a further modification of the sealing means for engaging a male condom.

DESCRIPTION OF THE PREFERRED EMBODIMENTS

Figure 1:
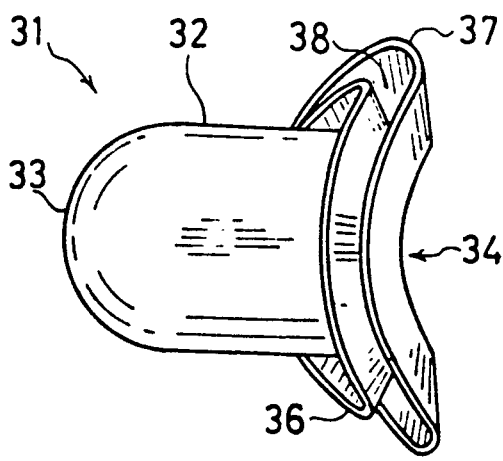
FIG. 1 is a perspective view of one embodiment of the condom for oral-genital use of the present invention.

The present invention generally comprises a condom designed to permit the practice of oral sex while preventing the transmission of venereal and other contagious diseases through oral-genital contact. With reference to FIGS. 1-5, one embodiment of the invention comprises a condom 31 which includes a tubular portion 32 having a rounded, closed end 33 and an opposed open end 34. The length of the tubular portion from the closed end 33 to the opening 34 is generally a few inches, and may be shorter than a typical prior art male condom. The tubular member adjacent to the opening 34 is formed with an oval, ellipsoid cross-section, and the opening end 34 describes a smoothly curved arc, with the arc extending in the same direction as the major axis of the ellipsoidal cross-section, as can been observed by comparing FIGS. 3 and 4. The tubular portion 32 may be provided with an expanded diameter adjacent to the closed end 33 and extending toward the open end, as shown in FIG. 2, to establish a non-constrictive fit with the male member.

Figure 6:
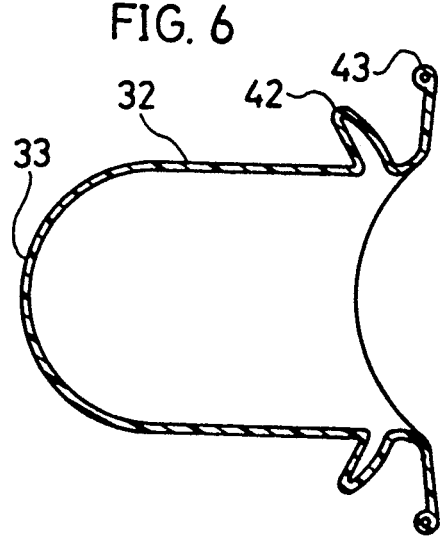
FIG. 6 is a cross-sectional elevation similar to FIG. 5, depicting a further development of the embodiment of FIGS. 1-5.

A significant feature of the condom 31 is the provision of a pair of flanges 36 and 37 disposed adjacent to the open end 34. The flanges 36 and 37 are closely spaced apart, and are defined as toroidal surfaces that are generally parallel. Both flanges are ovoid or elliptical when viewed in an end elevation (FIG. 4), and flange 36 is slightly smaller in major and minor axis dimensions. The flanges extend in outwardly flaring fashion toward the closed end 33, and there is defined between the flanges 36 and 37 a channel 38. The flanges 36 and 37 are each provided with a thickened rim 39 and 41, respectively, extending continuously about the distal edge portion of each flange to impart form-retaining characteristics to the flanges. The rims 39 and 41 maintain the open end of the condom and prevent collapse thereof, and maintain the parallel spacing and disposition of the flanges. In an alternative embodiment shown in FIG. 6, the distal edges of the flanges 36 and 37 are provided with a pair of O-Rings 42 and 43, respectively, each incorporated into one of the distal edges of one of the flanges. The O-Rings serve the same purposes as the rims 39 and 41.

The condom 31 may be formed of a pliant, thin, elastic, impervious material such as latex rubber, vinyl, or any similar non-toxic, non-allergenic, non-irritative material by multiple dipping processes, molding processes, or the like. With reference to FIG. 2, the majority of the tubular portion 32 is rather thin, on the order of 0.002–0.010 inch, whereas the end portion 44 of the tubular member adjacent to the open end 34 is thicker. One satisfactory version has an end portion thickness of 0.030 inch. The end portion 44, which flares slightly to join the flanges 36 and 37, is subject to the most stress and flexure of the assembly, and the thickness of this portion is increased proportionally.

Figure 7:
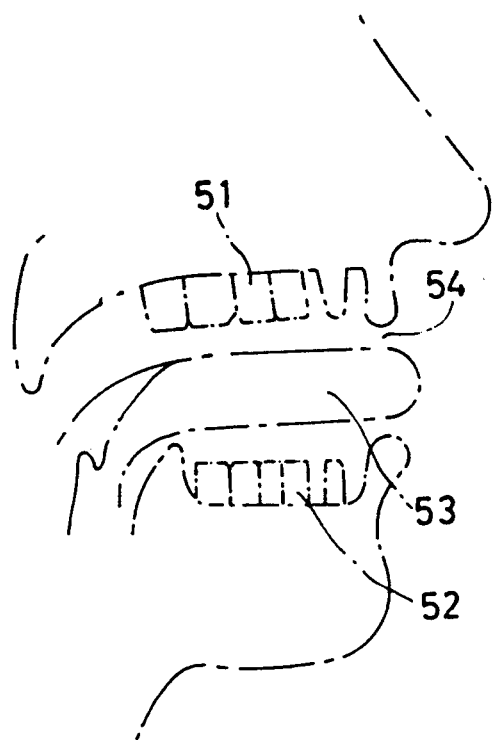
FIG. 7 is a cross-sectional schematic side view of the average human dentition and oral structure.
Figure 8:
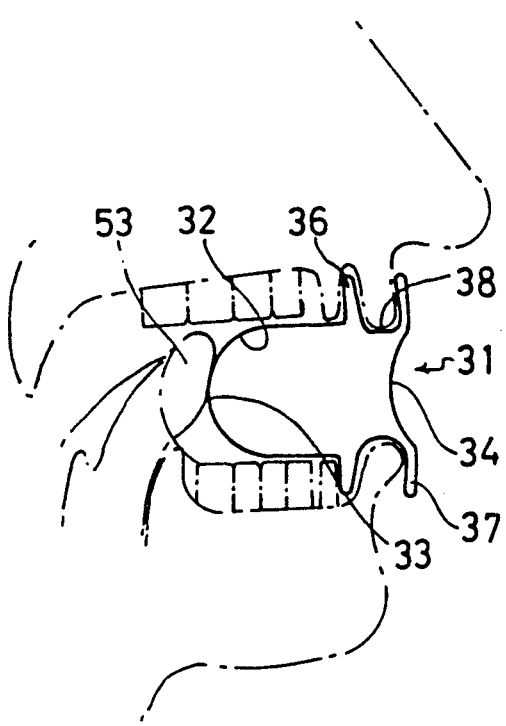
FIG. 8 is a cross-sectional view as in FIG. 7, showing the use of the embodiment of the condom of the present invention for fellatio.
Figure 10:
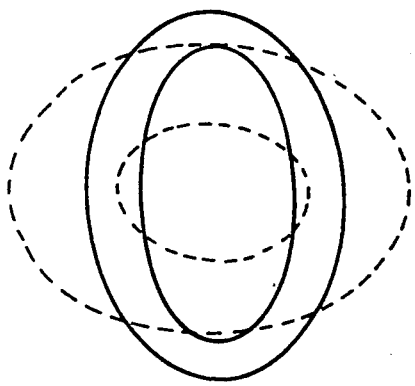
FIG. 10 is an end view of the condom of the present invention, as in FIG. 4, showing an alternative placement in the mouth.

The embodiments depicted in FIGS. 1–6 are designed to be used as shown in FIGS. 7 and 8. FIG. 7 shows a schematic cross-sectional elevation of the jaw area of a human head, including the upper jaw and teeth 51, the lower jaw and teeth 52, and the tongue 53 in the mouth 54. The condom 31 is applied to the mouth 54, with the closed end 33 and tubular portion 32 placed into the mouth. The condom 31 is oriented so that the upper and lower lips are engaged in the channel 38, preferably at opposite ends of the major axis of the ellipsoid formed by the opening 34. (Physiological variations may determine that the condom 31 is more easily used when oriented with upper and lower lips aligned with at opposite ends of the minor axis.) The jaws are closed slightly to squeeze the condom therebetween, deforming the ellipsoid into a more cylindrical shape, or further into a laterally extending ellipsoid, as shown in phantom line in FIG. 10.

The flange 37 is disposed outside of the lips of the condom user, and the flange 36 is disposed between the lips and teeth, as shown in FIG. 8. The open end 34 of the condom is directed outwardly to receive a penis for performing fellatio, and the length of the condom limits penetration of the penis to prevent triggering of the gag reflex. Furthermore, there is no interference with the nose of the condom user, so that the user may breathe freely. The condom permits fellatio while preventing skin-to-skin contact between the oral surfaces and the genital surfaces. After use, the condom 31 may be removed by grasping the outer flange 37 and pulling it from the mouth 54.

Figure 18:
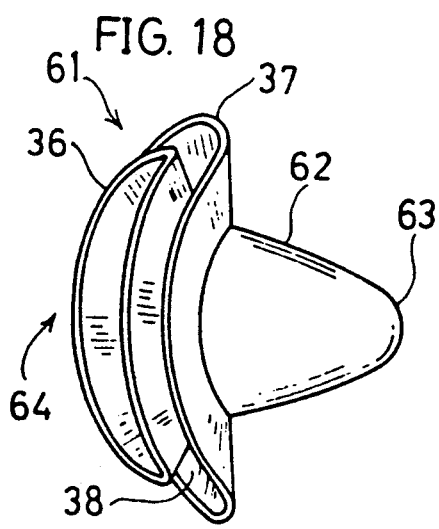
FIG. 18 is a perspective view of another embodiment of the invention, adapted for particular use in cunnilingus.
Figure 19:
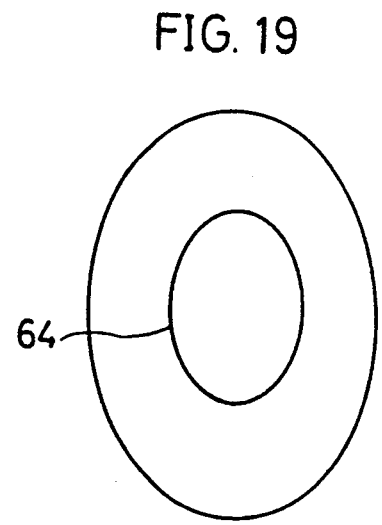
FIG. 19 is an end view of the embodiment shown in FIG. 18.
Figure 20:
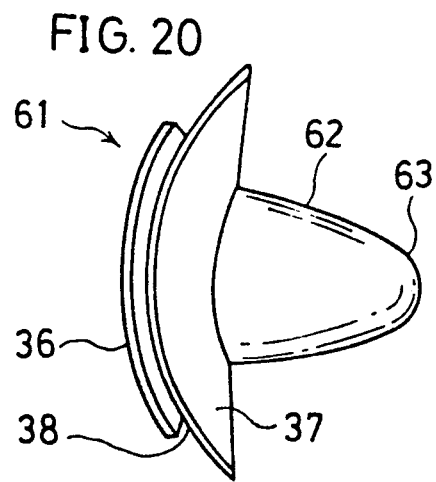
FIG. 20 is a side elevation of the embodiment shown in FIGS. 18 and 19.

A further embodiment of the present invention, shown in FIGS. 18–20, comprises a condom designed to permit the practice of cunnilingus while preventing skin-to-skin contact between oral and genital surfaces. (Throughout the description of the preferred embodiments, common reference numerals applied to different Figures and embodiments refer to the same structures.) The condom 61 includes a tapered, convex tubular portion 62 having a narrow, rounded closed end 63 and an open end 64. Joined to the tubular portion 62 adjacent to the open end 64 are a pair of flanges 36 and 37, as described previously, with a channel 38 defined therebetween. The flanges 36 and 37 are substantially the same as described previously, in form and function. The tubular portion 62 is formed of a similar material as described above.

Figure 9:
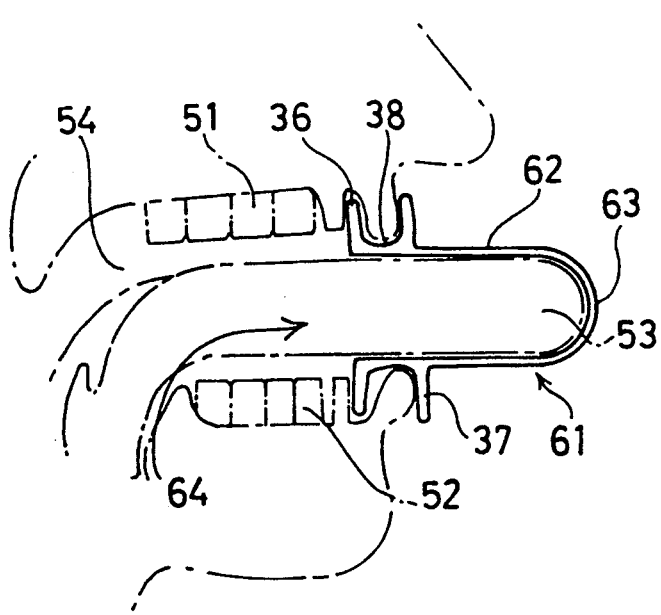
FIG. 9 is a cross-sectional view as in FIG. 7, showing the use of a further embodiment of the condom of the present invention for cunnilingus.

With regard to FIG. 9, the condom 61 is employed by being applied to the mouth 54, with the closed end 63 and tubular portion 62 placed outside the mouth. The condom 61 is oriented so that the upper and lower lips are engaged in the channel 38 at opposite ends of the major axis of the ellipsoid formed by the opening 64. The jaws are closed slightly to squeeze the condom therebetween, deforming the ellipsoid into a more cylindrical shape, or further into a laterally extending ellipsoid, as shown in phantom line in FIG. 10. The flange 37 is disposed outside of the lips of the condom user, and the flange 36 is disposed between the lips and teeth, as shown in FIG. 9. The tubular portion 62 extends outwardly, providing a sheath for the extended tongue 53 of the user. The condom 61 permits the user to perform cunnilingus while the tongue 53, lips, and surrounding area of the user are protected from contact with the vulva of the recipient. After use, the condom is removed by manually grasping the outer flange 37 and disengaging the dentition and lips from the flanges and channel 38.

Another embodiment of the invention, shown in FIGS. 11 and 12, comprises a condom 71 adapted to be applied to the penis and provide protection from disease transmission during fellatio and vaginal-penile intercourse. The condom 71 includes a shield 72 formed as an oval or ellipsoid planar member and fashioned of a form-retaining, impervious material. Alternatively, the shield may be curved out of the plane, as shown at 72' in phantom line, to conform to the curvature of the male genital area. The surface 73 of the shield 72 that contacts the skin of the male genital area, as well as the obverse surface, are preferably flocked or provided with a bonded fabric or similar surface treatment to prevent adhesion to the skin and pubic hair of both sex partners during fellatio and vaginal/penile intercourse. The shield includes a central opening 70 dimensioned to receive the penis therein.

The condom 71 further includes a tubular portion 74 extending from a junction with the opening 70 in the shield, the tubular portion 74 being formed of a thin, pliant, elastic, impervious material such as latex rubber or the like. The tubular portion 74 includes an enlarged distal end 76 provided to conform to the shape of the penis, and may optionally include an annular array 77 of longitudinally extending ribs. The ribs, which are molded directly into the tubular portion 74 adjacent to the shield 72, are provided to enhance the frictional engagement with the penis without hindering the loose fit of the distal end 76 on the penis. It may be appreciated that the loose fit is far more comfortable than the restrictive, elastic fit of commercial condoms, and far more pleasurable.

The device 71 additionally (and optionally) includes at least one annular, indented ring 75 disposed in the tubular portion 74. The rings 75 engage the male member at the base to prevent leakage of fluids from the condom. This sealing effect between the male member and the device may be augmented by the application of a waterproof, biologically safe, releasable adhesive to an annular portion of the tubular member adjacent to the rings 75. The adhesive acts synergistically to retain the condom on the male member, and to keep it safely on if the male erection is lost.

It may be appreciated that the condom 71 protects the two sex partners during fellatio by preventing skin-to-skin contact during the act. Furthermore, the shield 72 prevents accidental openings in the skin of the genital area, from such occurrences as an accidental plucking of a pubic hair when the condom is put on or removed. Such minor breaks in the skin can provide a vector for disease transmission through contaminated body fluids such as semen, saliva, or mucous. Indeed, the Director of Research for AIDS in the United States, Dr. Robert Gallo of the National Institute of Health, has stated that the plucking of a single pubic hair upon removal of a traditional condom is sufficient to break the skin-blood barrier at the base of the follicle socket. Also, it may be appreciated that the condom 71 may be used for intercourse, and will provide the same enhanced protection compared to a prior art male condom.

An alternative form of the embodiment of FIGS. 11 and 12, shown in FIGS. 13 and 14, includes the shield 72 as described previously and including the opening 70 therein. In this embodiment, there is no tubular portion secured permanently to the shield. Rather, there is provided an annular sealing ring 80 adapted to impinge on the shield 72, the ring 80 including a central opening 70' which registers with the opening 70 in the shield. The ring 80 is provided to form a releasable sealing engagement with a standard male condom, so that the assembly thereof may provide virtually the same protection from disease transmission as the previous embodiment.

The shield 72 is provided with an annular array of protrusions 78 disposed about the opening 70, each protrusion having an enlarged, ovoid head. The ring 80 is provided with an annular array of holes 79 disposed about the opening 70', each hole 79 being dimensioned to receive the head of one protrusion in snap-fit, releasable fashion. The protrusions 78 and holes 79 are engageable to join the ring 80 to the shield 72 in direct impingement therewith, with a male condom secured therebetween. As shown in FIG. 15, the shield 72 may be provided with a groove 81 extending about the opening 70, and disposed to receive the rolled (or unrolled) edge 82 of a typical prior art male condom 83. The compression of the junction of the shield 72 and ring 80, together with the engagement of the condom edge 82 in the groove 81 forms a tight seal between the shield and the condom to prevent contamination of the skin of the genital area. The condom 83 may be unrolled from its packaged state to the extent necessary to cover the penis, so that fellatio may be performed, or much less of the condom 83 may be unrolled, and the assembly may be used for cunnilingus. As in the previous embodiment, the assembly may also be used to perform intercourse, with the added protection of the shield 72.

In a further modification of the shield and condom assembly, shown in FIG. 16, there is provided a shield 72 with central opening 70, and a sealing ring 80, as described previously. The annular groove 81 for receiving the edge of a male condom is spaced outwardly from the opening 70, and a snap groove 86 is provided in the shield 72, spaced concentrically about the opening 70 and within the groove 81. The sealing ring 80 is provided with an annular snap flange 87 disposed about the opening 70' and dimensioned to snap-engage in the groove 86 with an annular portion of the condom 83 entrained therebetween, in the fashion of a Ziploc ™ fastener. The continuous seal formed by the engagement of the groove 86 and flange 87, together with the engagement of the condom therein, provides a more fluid-tight, leakproof seal to prevent contamination of either partner by body fluids.

In the modification depicted in FIG. 17, the assembly of FIG. 16 is changed only to the extent that the sealing ring 80 and the shield 72 are joined at an annular junction 88 spaced radially from the openings 70 and 70' to form a unitary shield assembly. This form of the invention prevents accidental loss of the sealing ring 80.

With regard to the embodiments shown in FIGS. 14-17, a commercially available male condom may be joined to the assembly of the shield 72 and sealing ring 80, and used for the purpose of performing fellatio and sexual intercourse. After use, the ring 80 may be separated from the shield 72, the condom may be discarded, and the shield and ring may be cleaned for reuse. In this manner the safety of available male condoms may be enhanced for fellatio and intercourse.

Figure 26:
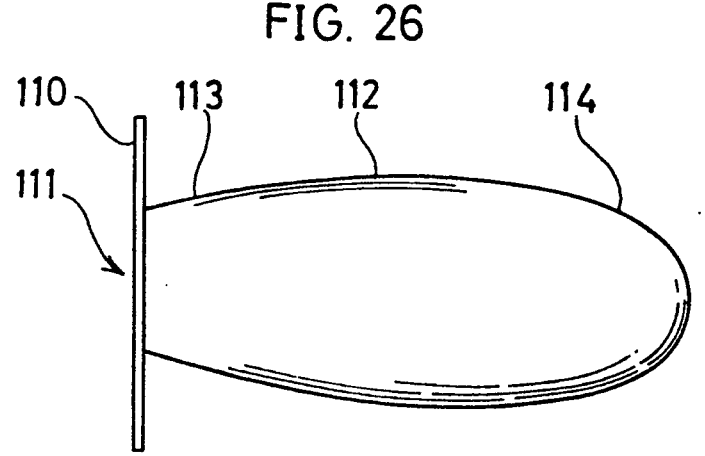
FIG. 26 is a side elevation of a further embodiment of the invention, comprising a loose-fitting prophylactic condom adapted for use for fellatio.

Another embodiment of the invention, shown in FIG. 26, carries forth two important concepts of the present invention. The embodiment includes a shield 110 comprising a planar ellipsoid formed of a flexible, form-retaining, fluid impervious material such as latex rubber, polymer plastic, or the like. The shield includes a central opening 111 which is dimensioned to be wider in diameter than the base of the average penis. The device includes a tubular member 112 having an open end 113 secured and sealed about the central opening 111 of the shield, and a rounded, closed distal end 114. The tubular member has the configuration of a prolate spheroid, forming a non-constricting enclosure about the penis. This embodiment is adapted for performing fellatio with maximum comfort and pleasurable stimulation, due to the non-constrictive fit. Furthermore, there is no need for any constrictive engagement of the penis, due to the fact that fellatio does not generally cause removal of the condom from the penis. Moreover, the movement of the loose tubular member against the penis heightens sensual contact.

Figure 21:
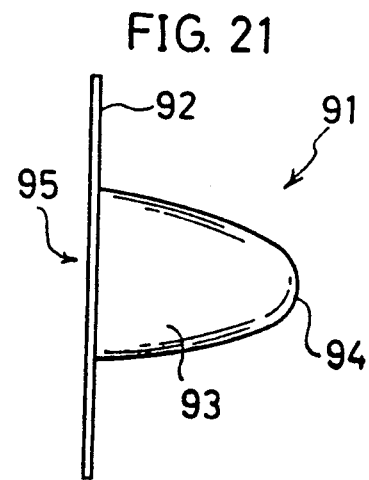
FIG. 21 is a side elevation of a further embodiment of the invention, adapted for use in cunnilingus.

In a further embodiment of the invention, shown in FIG. 21, there is provided a condom 91 adapted for cunnilingus. The condom 91 includes an shield 92 defined by an oval, generally planar member fabricated of a pliant, impervious material such as latex or the like. The shield includes a central opening 95, and a tapered tubular portion 93 extends outwardly from the opening 95. The tubular portion 93 has a rounded end 94, and is formed of thin, elastic, impervious material. The shield 92 is sufficiently large to cover the mouth and surrounding area of the user, and is held in place manually. The tongue of the user may be extended into the tubular portion 93 for the purpose of performing cunnilingus without direct skin-to-skin contact between the oral surfaces and the vulva, and without any contamination by exchange of body fluids.

Figure 2:
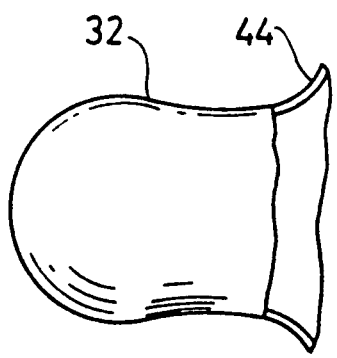
FIG. 2 is a fragmentary, partially broken away view of the tubular portion of the embodiment of the invention shown in FIG. 1.
Figure 3:
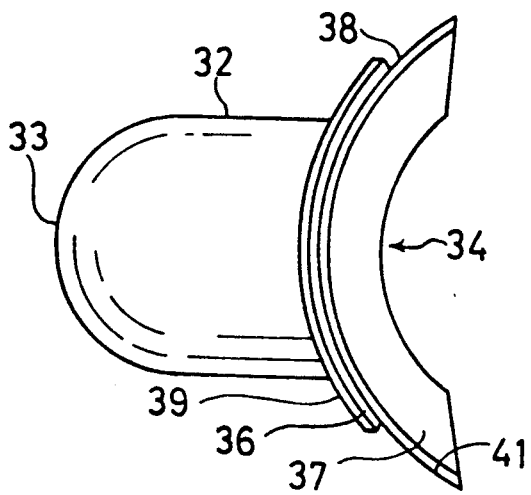
FIG. 3 is a side elevation of the embodiment of the invention shown in FIGS. 1 and 2.
Figure 4:
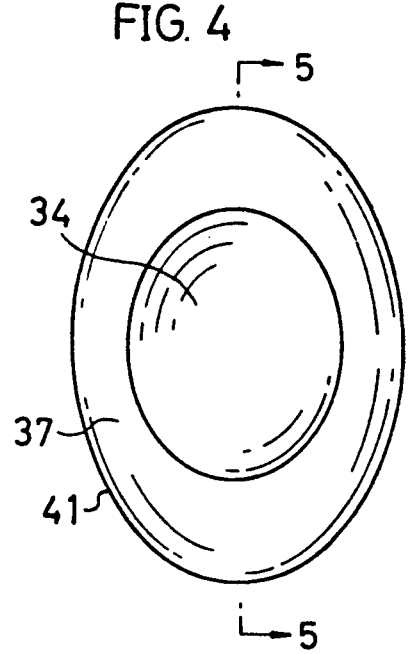
FIG. 4 is an end elevation of the embodiment shown in FIGS. 1-3.
Figure 5:
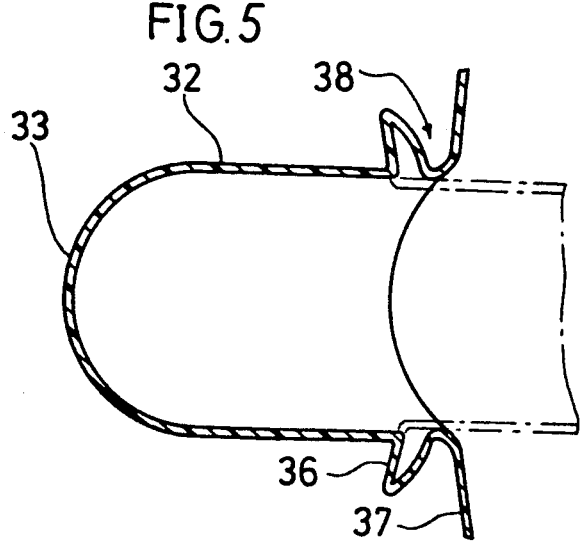
FIG. 5 is a cross-sectional elevation taken along line 5—5 of FIG. 4.
Figure 22:
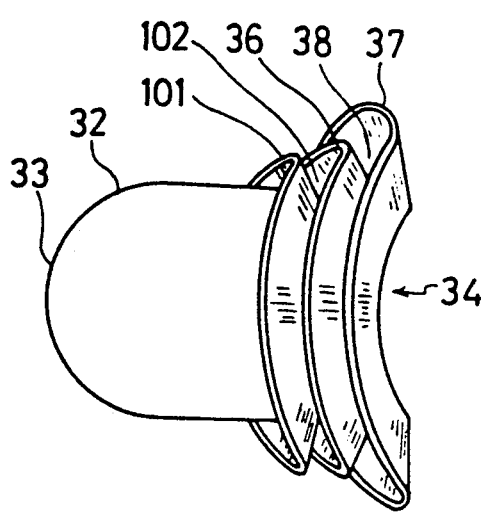
FIG. 22 is a perspective view of another embodiment of the invention adapted for fellatio.

Another embodiment of the invention, depicted in FIG. 22, is similar in many aspects to the embodiment of FIGS. 1 and 3, and common reference numerals are used to designate common features. This embodiment includes a tubular portion 32 having a rounded, closed end 33 and an opposed open end 34. The length of the tubular portion from the closed end 33 to the opening 34 is generally a few inches, and may be shorter than a typical prior art male condom. The tubular member adjacent to the opening 34 is formed with an oval, ellipsoid cross-section, and the opening end 34 describes a smoothly curved arc, with the arc extending in the same direction as the major axis of the ellipsoidal cross-section. As described previously, a pair of flanges 36 and 37 are disposed adjacent to the open end 34. The flanges 36 and 37 are closely spaced apart, and are defined as toroidal surfaces that are generally parallel. The flanges extend in outwardly flaring fashion toward the closed end 33, and there is defined between the flanges 36 and 37 a channel 38.

Figure 23:
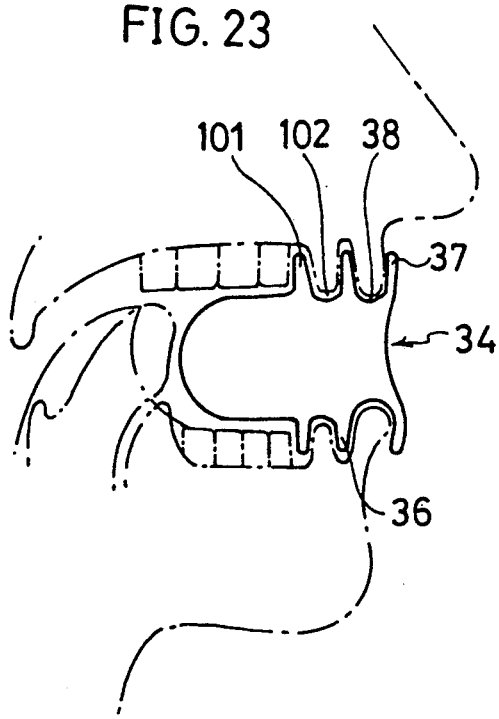
FIG. 23 is a cross-sectional view as in FIG. 7, showing the use of the embodiment of FIG. 22 of the present invention for fellatio.

The embodiment of FIG. 22 further includes a third flange 101, extending parallel to the flanges 36 and 37 and spaced apart and adjacent to flange 36. The flanges 101 and 36 define therebetween a channel 102 extending about the condom parallel to the channel 38. As depicted in FIG. 23, the channel 38 is engaged by the lips of the user, and the channel 102 is disposed to be engaged by the front teeth of the user, providing greater retention of the condom in the oral cavity with less effort by the lips. As noted with regard to FIGS. 1-3, the condom of FIGS. 22 and 23 eliminates skin-to-skin contact during fellatio.

Figure 24:
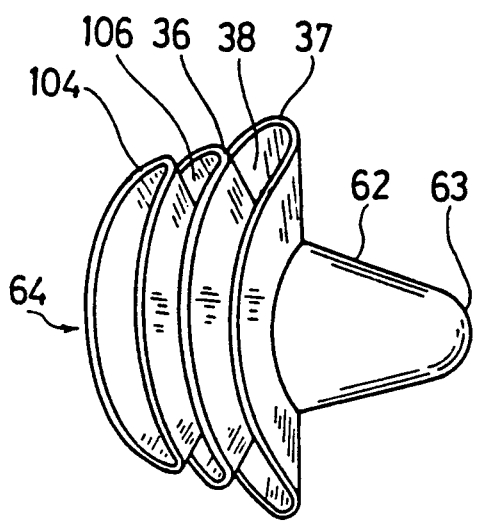
FIG. 24 is a perspective view of another embodiment of the invention adapted for cunnilingus.

A further embodiment of the invention, depicted in FIG. 24, is similar in many aspects to the embodiment of FIGS. 18-20, and common reference numerals are used to designate common features. This embodiment includes a tapered tubular portion 62 having a narrow, rounded closed end 63 and an open end 64. Joined to the tubular portion 62 adjacent to the open end 64 are a pair of flanges 36 and 37, as described previously, with a channel 38 defined therebetween. The flanges 36 and 37 are substantially the same as described previously, in form and function. The tubular portion 62 is formed of a similar material as described above. Also provided is a third flange 104, extending parallel to the flanges 36 and 37 and disposed adjacent to and spaced apart from the flange 36. The flanges 36 and 104 define therebetween a channel 106 extending about the condom.

Figure 25:
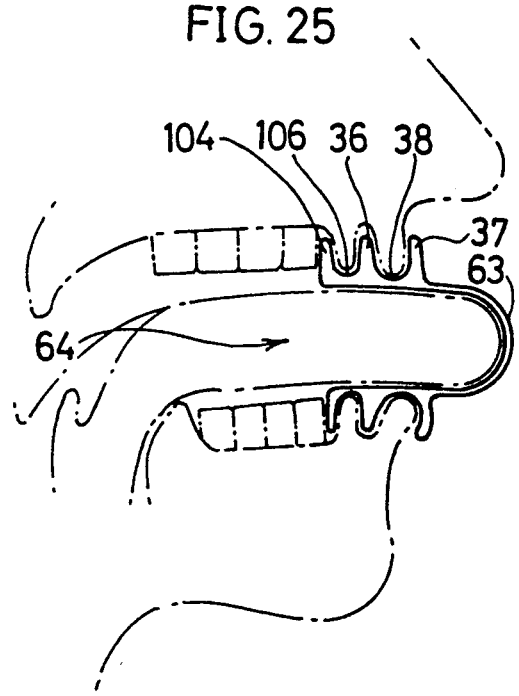
FIG. 25 is a cross-sectional view as in FIG. 7, showing the use of the embodiment of FIG. 24 of the present invention for cunnilingus.

As shown in FIG. 25, the condom of FIG. 24 is adapted to be applied to the oral cavity, with the upper and lower lips disposed in the channel 38 and the upper and lower front teeth disposed in the channel 106. The portion 62 extends outwardly from the mouth, and provides a sheath within which the tongue may be extended for performing cunnilingus and similar sexual acts. The channel 106 permits greater retention of the condom in the mouth without significant effort by the lips of the user.

It may be appreciated that all embodiments of the present invention are directed toward facilitating the safe practice of oral sex. To further this goal, any of the embodiments may be packaged together with substances that impart a pleasing flavor and aroma to the condom, so that the use thereof will not be hindered by unpleasant taste or scent. In addition, coloring and surface texture may be added to the condoms to enhance the pleasure of their use.

We claim:

1. A condom for oral-genital use, including first means for removably securing said condom to the mouth of a person practicing oral sex and a tubular portion secured to said first means, both said first means and said tubular portion being disposed to form a barrier between the mouth and the genital surfaces of the person receiving oral sexual stimulation, said tubular portion including an open end at which said first means is situated and a closed distal end situated at the end of said tubular portion that is opposite from said open end thereof, wherein said first means includes a first annular flange extending around the circumference of said open end of said tubular portion and adapted to impinge on the outer lip surfaces of the mouth of the condom user, wherein said first means further includes a second annular flange extending around the circumference of said tubular portion adjacent to said first flange and defining therebetween an annular channel, said annular channel being adapted to receive the lips of the condom user to retain said condom within the mouth, each of said first and second flanges being formed of resilient material and being continuous around the circumference of said tubular portion to completely encircle said tubular portion in the region of said open end thereof.

2. The condom of claim 1, wherein said first and second flanges are disposed in generally parallel, spaced apart fashion, said flanges extending outwardly from said tubular portion and flaring towards said distal, closed end.

3. The condom of claim 1, wherein said flanges are formed of a pliant, form-retaining, impervious material, and said tubular portion is formed of a pliant, thin, elastic, impervious material, said flanges being joined to said tubular portion in continuous, sealing engagement.

4. The condom of claim 1, wherein said second flange is dimensioned to be received within the lips of the mouth of the condom user.

5. The condom of claim 1, wherein said tubular portion extends from a junction with said flanges inwardly into the mouth of the condom user.

6. The condom of claim 1, wherein said tubular portion and said flanges extend about a common axis of symmetry, and said flanges define toroidal surfaces about said axis of symmetry.

7. The condom of claim 6, wherein said flanges define an ovoid shape in a plane intersecting said axis of symmetry and extending orththogonal thereto, said ovoid shape having major and minor axes, said annular channel including opposed portions intersected by said major axis which are adapted to be engaged by the lips and mouth of the condom user and compressed by partial closure of the jaws of the user to retain said condom within the mouth.

8. A condom suitable for oral-genital use, comprising an elongated tubular body closed at one end and open at the other end; said tubular body being made of a flexible material impermeable to liquids; and first and second annular flanges positioned near the open end of said tubular body and spaced apart from each other; said annular flanges and tubular body being adapted to engage the lips of a user for oral-genital use and operating with the lips to prevent the flow of liquids into the mouth of the user.

9. The condom as claimed in claim 8, wherein said tubular body is made from a non-toxic, non-allergenic, non-irritative material.

10. The condom as claimed in claim 8, wherein said tubular body is made latex rubber or vinyl 11. The condom as claimed in claim 8, wherein said tubular body has an overall length sufficiently short to minimize the inadvertent triggering of the gag reflex of the user during the use of the condom.

12. The condom as claimed in claim 8, wherein said tubular body is thicker near the open end relative the closed end.

13. The condom as claimed in claim 8, wherein said tubular body has a diameter which increases from the open end towards the closed end.

14. The condom as claimed in claim 8, wherein said tubular body is made from a material having a thickness from about 0.002 inch to about 0.010 inch.

15. A condom for oral-genital use, including first means for removably securing said condom to the mouth of a person practicing oral sex and a tubular portion secured to said first means, both said first means and said tubular portion being disposed to form a barrier between the mouth and the genital surfaces of the person receiving oral sexual stimulation, said tubular portion having an open end at which said first means is situated and a closed distal end situated at the end of said tubular portion that is opposite from said open end, wherein said first means includes a first annular flange extending around the circumference of said open end of said tubular point and adapted to impinge on the outer lip surfaces of the mouth of the condom user, and wherein said first means further includes a second annular flange extending around the circumference of said tubular portion adjacent to said first flange and defining therebetween an annular channel, said annular channel being adapted to receive the lips of the condom user to retain said condom within the mouth, each of said first and second flanges being formed of resilient material and being continuous around the circumference of said tubular portion to completely encircle said tubular portion in the region of said open end thereof, wherein said tubular portion is adapted to extend from a junction with said flanges outwardly from the mouth of the condom user, said tubular portion being dimensioned to receive the extended tongue of the condom user.

* * * * *